US00PP20933P2

(12) United States Plant Patent

Noodelijk

(10) Patent No.: US PP20,933 P2

(45) Date of Patent: Apr. 13, 2010

(54) *CHRYSANTHEMUM* PLANT NAMED 'TWINO BRONZE'

(50) Latin Name: *Chrysanthemum morifolium*
Varietal Denomination: Twino Bronze

(76) Inventor: Robert Noodelijk, Vrouwgeestweg 26, Woubrugge (NL) 2481 KN ( * ) Notice: Subject to any disclaimer, the term of this patent is extended or adjusted under 35 U.S.C. 154(b) by 0 days.

(21) Appl. No.: 12/316,928

(22) Filed: Dec. 18, 2008

(51) Int. Cl.
*A01H 5/00* (2006.01)

(52) U.S. Cl. ..... Plt./296

(58) Field of Classification Search ..... Plt./296
See application file for complete search history.

*Primary Examiner*—Susan B McCormick Ewoldt
(74) *Attorney, Agent, or Firm*—Jondle & Associates, P.C.

(57) ABSTRACT

A *chrysanthemum* plant named 'Twino Bronze' characterized by small-sized blooms with yellow-orange ray florets with bronze-orange centers, prolific branching, a natural season flowering date of October 10, a blooming period of 4 to 5 weeks, a rounded plant habit and a spreading growth habit, is disclosed.

1 Drawing Sheet

Genus: *Chrysanthemum morifolium.*
Variety denomination: 'Twino Bronze'.

BACKGROUND OF THE INVENTION

'Twino Bronze' is a product of a breeding and selection program for outdoor pot mums (garden mums) which had the objective of creating new *chrysanthemum* cultivars with a decorative type inflorescence, a natural season flowering date around October 10 and a blooming period of 4 to 5 weeks. The new plant of the present invention comprises a new and distinct cultivar of *chrysanthemum* plant.

'Twino Bronze' is a seedling resulting from the open pollination conducted in September 2005 among groups of unnamed and unpatented *chrysanthemum* cultivars maintained under the control of the inventor for breeding purposes. The new and distinct cultivar was discovered and selected as one flowering plant by Rob Noodelijk on a cultivated field in Woubrugge, The Netherlands in September 2006. 'Twino Bronze' was first asexually reproduced by cuttings in greenhouses at Woubrugge, The Netherlands in January 2007 and has been asexually reproduced over an approximately two-year period. The new cultivar has been found to retain its distinctive characteristics through successive asexual propagations.

SUMMARY OF THE INVENTION

The following are the most outstanding and distinguishing characteristics of the new cultivar when grown under normal horticultural practices in Woubrugge, The Netherlands.

1. Small yellow-orange inflorescences with orange-bronze centers;
2. Very prolific branching; and
3. A rounded plant habit.

DESCRIPTION OF THE PHOTOGRAPHS

The present invention of a new and distinct variety of *chrysanthemum* is shown in the accompanying photographs, the colors being as nearly true as possible with color photographs of this type. The photographs are of a plant that has been in bloom for approximately 3 weeks.

DESCRIPTION OF THE INVENTION

Figure 1:
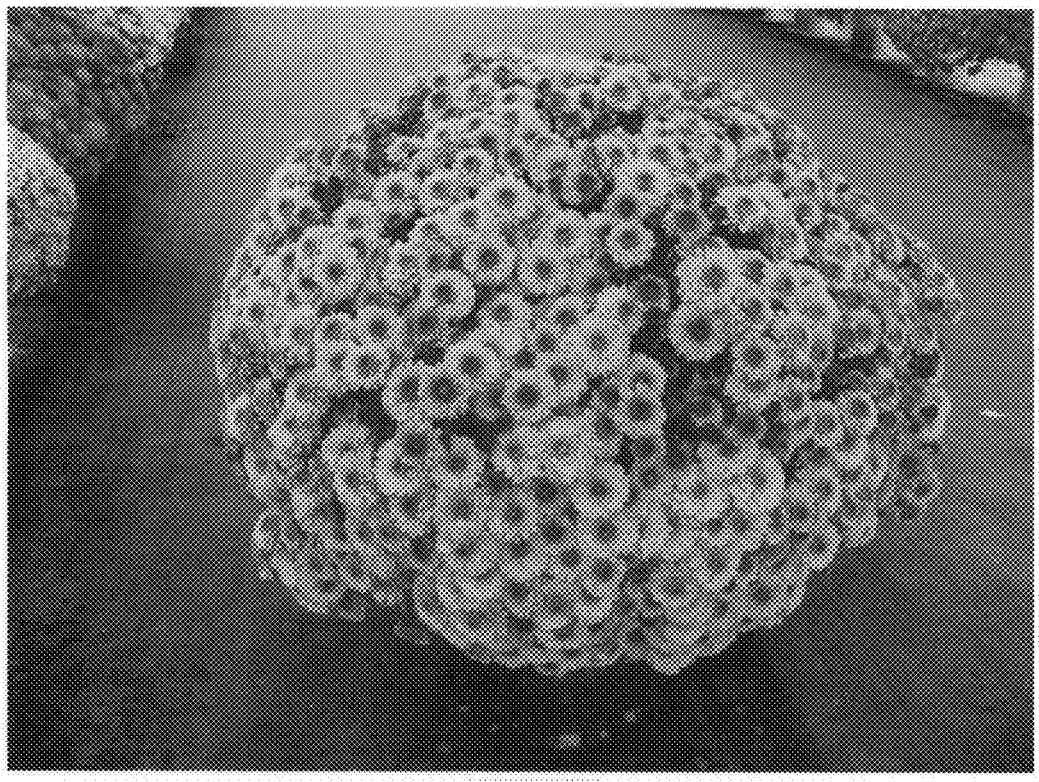
FIG. 1 shows a plant of the cultivar in full bloom.
Figure 2:
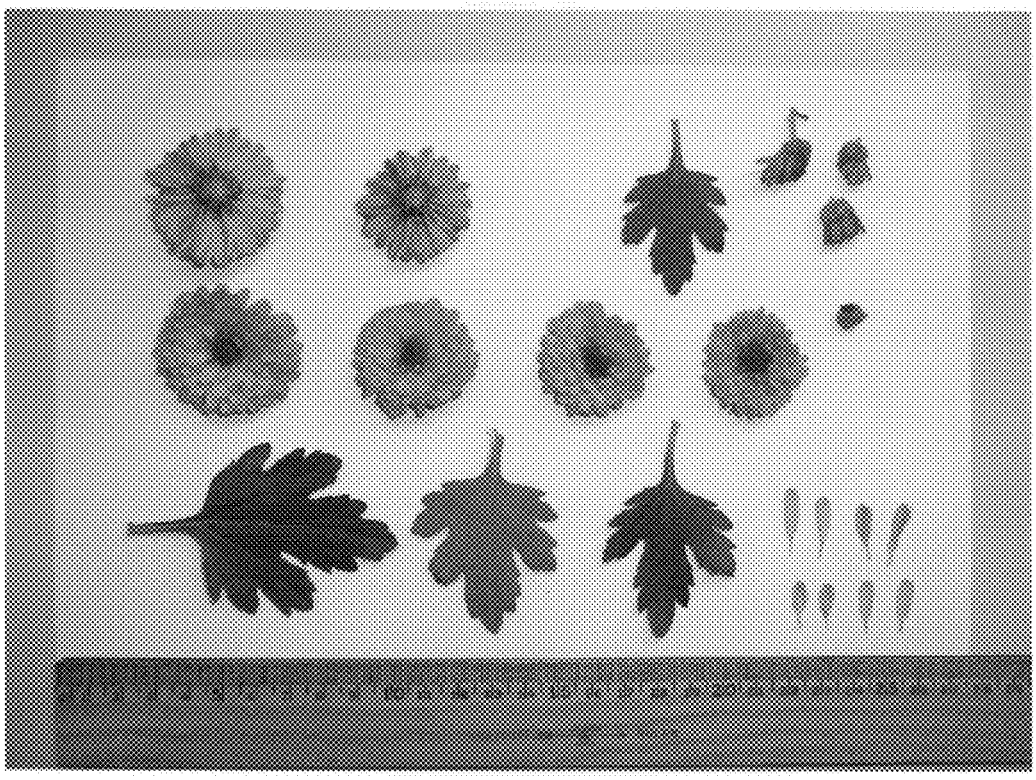
FIG. 2 shows a close-up of the buds, florets, leaves and individual inflorescences.

This new variety of *chrysanthemum* is of the botanical classification *Chrysanthemum morifolium*. The observations and measurements were gathered from plants grown outdoors in Woubrugge, The Netherlands under natural day length and temperatures and planted in week 22 in 2006 and 2007. The average natural blooming date of this crop was October 10. The average height of the plants was 37 cm. No growth retardants were used. No tests were done on disease or insect resistance or susceptibility. No tests were done on cold or drought tolerance. This new variety produces small-sized blooms with yellow-orange ray florets and bronze-orange centers and a blooming period of 4 to 5 weeks.

The following is a description of the plant and characteristics that distinguish 'Twino Bronze' as a new and distinct variety. The color designations are taken from the plant itself. Accordingly, any discrepancies between the color designations and the colors depicted in the photographs are due to photographic tolerances. The color chart used in this description is The Royal Horticultural Society Colour Chart, edition 1995.

DETAILED BOTANICAL DESCRIPTION

Plant:

*Shape.*—Rounded.
*Growth habit.*—Spreading.
*Growth rate.*—Slow.
*Height.*—35 cm to 40 cm.
*Width.*—40 cm to 50 cm.

Branches:

*Stem.*—Color: RHS 139C (Green). Strength: Strong. Brittleness: Branches are not brittle. Anthocyanin coloration: Absent.

*Length of lateral branch* (*from top to bottom*).—20 cm to 25 cm.
*Diameter of lateral branch.*—0.3 cm.
*Lateral branch color.*—RHS 139C (Green).
*Lateral branch attachment.*—Petiolate.
*Branching* (*average number of lateral branches*).—Very prolific with 14 breaks after pinching.

Leaves:
*Color.*—Upper surface: RHS 137A (Green). Lower surface: RH 137C (Green).
*Size.*—General: Medium. Length: 5.0 cm to 7.0 cm. Width: 4.0 cm to 6.0 cm.
*Quantity* (*number per lateral branch*).—7 to 12.
*Shape.*—Ovate.
*Apex.*—Acute.
*Base.*—Asymmetric.
*Margin.*—Cleft.
*Texture.*—Upper surface: Glabrous. Lower surface: Pubescent.
*Venation arrangement.*—Pinnate.
*Shape of base of sinus between lateral lobes.*—Acute.
*Margin of sinus between lateral lobes.*—Mostly diverging and sometimes converging.

Bud:
*Size.*—General: Small. Cross-section: 0.8 cm to 1.0 cm. Height: 0.6 cm.
*Outside color.*—RHS 185A (Greyed-purple).
*Involucral bracts.*—3 rows, length is 0.7 cm, width is 0.3 cm.
*Involucral bracts among disc-florets.*—Absent.
*Involucral bracts color.*—RHS 139B (Green).

Bloom:
*Type.*—Decorative.
*Size.*—General: Small. Fully expanded: 3.1 cm to 4.0 cm.
*Number of blooms per branch.*—Approximately 8 to 10 per branch.
*Performance on the plant* (*blooming period*).—4 to 5 weeks.
*Fragrance.*—Typical of *chrysanthemum,* slight.
*Tonality from distance.*—A very rich flowering garden mum with small yellow-orange inflorescences with bronze-orange centers.
*Discoloration to color.*—RHS 15D (Light yellow-orange).
*Peduncle.*—Length: 4.2 cm to 7.0 cm. Diameter: 0.2 cm. Color: RHS 138B (green).
*Natural season blooming date.*—October 10.

Ray florets:
*Texture.*—Both the upper and lower surfaces are smooth.
*Number.*—170 to 200.
*Cross-section.*—Flat to concave.
*Longitudinal axis of majority.*—Straight.
*Length of corolla tube.*—0.4 cm to 0.5 cm.
*Apex.*—Emarginate.
*Margin.*—Entire.
*Length.*—1.1 cm to 1.4 cm.
*Width.*—0.5 cm.
*Ratio length/width.*—Medium.
*Color.*—Upper surface of the outer ray-florets: RHS 15B (Yellow-orange). Lower surface of the ray-florets: RHS 26A (Orange).

Disc florets:
*Disc diameter.*—0.3 cm to 0.5 cm.
*Disc length.*—0.4 cm.
*Distribution of disc florets.*—Very few, 5 to 26 per disk, visible only at very late stages of blooming.
*Shape.*—Tubular.
*Color.*—RHS 16A (Yellow-orange).
*Receptacle shape.*—Conical and flat.
*Color of center of the flower* (*disc-florets*).—Immature: RHS 16A (Yellow-orange). Mature: RHS 16A (Yellow-orange).

Reproductive organs:
*Stamen* (*present in disc florets only*).—Thin, 0.2 cm to 0.3 cm.
*Stamen color.*—RHS 14A (Yellow-orange).
*Pollen amount.*—Sparse and appears in a very late stage.
*Pollen color.*—RHS 14A (Yellow-orange).
*Style appearance.*—Thin.
*Style color.*—RHS 1A (Yellow-green).
*Style length.*—0.3 cm.
*Stigma color.*—RHS 3A (Yellow-green).
*Stigma width.*—0.25 cm.
*Ovaries.*—Enclosed in calyx.

Fruit/seed set: None observed.

COMPARISON WITH COMMERCIAL CULTIVARS

'Twino Bronze' differs from the commercial variety 'Katelli' (U.S. Plant Pat. No. 16,674) in that 'Twino Bronze' blooms later (October 10) than 'Katelli' (September 13–20). Additionally, 'Twino Bronze' has less ray florets (170 to 200) and leaves per lateral branch (7 to 12) than 'Katelli' (has 240 to 250 ray florets and 25 leaves per branch).

I claim:

1. A new and distinct variety of *chrysanthemum* plant as described and illustrated.

* * * * *